(12) United States Patent
Murdeshwar et al.

(10) Patent No.: US 11,832,869 B2
(45) Date of Patent: Dec. 5, 2023

(54) RESISTIVE HEAT ABLATION FOR TREATMENT OF THE ANATOMY

(71) Applicant: GYRUS ACMI, INC., Southborough, MA (US)

(72) Inventors: Nikhil M. Murdeshwar, Maple Grove, MN (US); Timothy Ozell, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 523 days.

(21) Appl. No.: 16/291,140

(22) Filed: Mar. 4, 2019

(65) Prior Publication Data

US 2020/0281639 A1    Sep. 10, 2020

(51) Int. Cl.
*A61B 18/00* (2006.01)
*A61B 18/04* (2006.01)
*A61B 18/08* (2006.01)

(52) U.S. Cl.
CPC .. *A61B 18/082* (2013.01); *A61B 2018/00232* (2013.01); *A61B 2018/00559* (2013.01); *A61B 2018/00577* (2013.01); *A61B 2018/046* (2013.01)

(58) Field of Classification Search
CPC ........ A61B 18/082; A61B 2018/00232; A61B 2018/00559; A61B 2017/4216; A61B 18/08; A61B 18/04
See application file for complete search history.

(56) References Cited

U.S. PATENT DOCUMENTS

| | | | |
|---|---|---|---|
| 4,949,718 A * | 8/1990 | Neuwirth | A61B 18/00 607/105 |
| 7,211,079 B2 | 5/2007 | Treat | |
| 9,084,609 B2 * | 7/2015 | Smith | A61B 18/1492 |
| 2002/0045893 A1 * | 4/2002 | Lane | A61B 18/02 606/21 |
| 2005/0182397 A1 | 8/2005 | Ryan | |
| 2008/0243103 A1 | 10/2008 | Whetham et al. | |
| 2011/0264039 A1 | 10/2011 | Thielen et al. | |
| 2013/0172877 A1 | 7/2013 | Subramaniam et al. | |

(Continued)

FOREIGN PATENT DOCUMENTS

| | | |
|---|---|---|
| CN | 111643180 A | 9/2020 |
| EP | 3456278 A2 | 3/2019 |

(Continued)

OTHER PUBLICATIONS

"European Application Serial No. 20159849.7, Extended European Search Report dated Jul. 20, 2020", 7 pgs.

(Continued)

*Primary Examiner* — Joseph A Stoklosa
*Assistant Examiner* — Annie L Shoulders
(74) *Attorney, Agent, or Firm* — Schwegman Lundberg & Woessner. P.A.

(57) ABSTRACT

A medical device that includes an expandable member, a fluid lumen, and a heating element. The expandable member has an inner expandable member and an outer expandable member. The fluid lumen is between the inner expandable member and the outer expandable member. The heating element is located inside of the fluid lumen.

14 Claims, 2 Drawing Sheets

(56) References Cited

U.S. PATENT DOCUMENTS

| | | | | |
|---|---|---|---|---|
| 2014/0018794 A1* | 1/2014 | Anderson | .......... | A61B 18/1492 |
| | | | | 606/41 |
| 2017/0367760 A1* | 12/2017 | Crozier | .............. | A61B 18/1815 |
| 2020/0060942 A1* | 2/2020 | Rajagopalan | ............ | A61B 5/42 |

FOREIGN PATENT DOCUMENTS

| WO | WO-0000100 A1 * | 1/2000 | ............. A61B 18/08 |
|---|---|---|---|
| WO | WO-0000100 A1 | 1/2000 | |
| WO | WO-2016176567 A1 * | 11/2016 | ......... A61B 18/1492 |
| WO | WO-2016176567 A1 | 11/2016 | |

OTHER PUBLICATIONS

"European Application Serial No. 20159849.7, Response filed Mar. 5, 2021 to Extended European Search Report dated Jul. 20, 2020", 10 pgs.

\* cited by examiner

RESISTIVE HEAT ABLATION FOR TREATMENT OF THE ANATOMY

FIELD

These teachings relate to a medical device for treating the anatomy and a method thereof

BACKGROUND

Menorrhagia is a medical condition that includes abnormally heavy and prolonged menstrual bleeding and pain. For decades, hormone pills and/or hysterectomy were used to treat menorrhagia.

Recently, medical devices have been introduced to treat menorrhagia by way of endometrium ablation, where the endometrium is exposed to various treatment modalities such as RF energy, cryogenics, thermal energy, microwave energy, and/or steam.

While often effective, some medical devices include some shortcomings.

For example, some medical devices require a user to wiggle or manipulate the medical device inside the body cavity to spread the ablation; however, such wiggling or manipulation may result in tissue perforation, user discomfort, may prolong a medical procedure, and/or may cause fatigue to the user.

For example, some medical devices include an electrode array; however, inserting an electrode array into a body cavity risks tissue perforation.

For example, some medical devices utilize a fluid that is circulated inside of single-walled balloon. However, circulating a fluid inside of a single-walled balloon risks fluid entering the body cavity if the balloon breaks or leaks.

Some examples of medical devices are disclosed in U.S. Pat. No. 7,211,079, US 20130172877, and US 20080243103, the disclosures of which are hereby incorporated by reference herein for all purposes.

It may be desirable to have a medical device that is able to overcome at least one of the aforementioned difficulties.

SUMMARY

A medical device is disclosed. The medical device according to these teachings overcomes as least some of shortcomings discussed in the background section of this application.

A medical device is disclosed that includes an expandable member, a fluid cavity, and a heating element. The expandable member has an inner expandable member and an outer expandable member. The fluid cavity is defined between the inner expandable member and the outer expandable member. One or more heating elements are located inside of the fluid cavity.

A medical device is disclosed that includes an introducer, expandable member, and a heating element. The expandable member is connected to the introducer, the expandable member comprises an outer surface. The heating element is disposed on the outer surface of the expandable member. The introducer is configured to be at least partially inserted into a body cavity.

A medical device is disclosed that includes expandable member; a fluid cavity, and a heating element. The fluid cavity is located inside of the expandable member. The fluid cavity is configured to connect to a fluid source to supply a fluid into the fluid cavity. The heating element is configured to connect to a power source to supply power to the heating element to generate heat.

DETAILED DESCRIPTION

These teachings relate to a medical device. The medical device may be used to treat or effect an anatomical feature. The medical device may be configured to treat an anatomical feature by way of ablation. The medical device may be configured to effect or destroy an anatomical feature, such as the endometrium with heat. The anatomical feature may be any anatomical feature, such as a body cavity or a body lumen. The body cavity may be a uterus. The medical device may be configured to treat menorrhagia.

While the medical device disclosed herein may be used to treat menorrhagia, it is understood that the medical device can be used in other applications as well. For example, the device and system can be used to treat tissue in the bladder, vagina, esophagus, trachea, urethra, ureter, prostate gland, kidney, intestinal growths or abnormal tissues of the intestine, cancerous tissue, etc.

The medical device comprises a hand piece. The hand piece may function to be held by a user or robot and/or support or contain one or more components of the medical device. For example, the hand piece may support or contain one or more elements or devices for treating the anatomy and/or for operating the medical device. For example, the hand piece may house or contain the fluid source, the power source, the second fluid source, or a combination thereof. Stated another way, the fluid source and/or the second fluid source may be a container or receptacle located within the hand piece or introducer. In other configurations, the hand piece or the introducer may comprise the fluid connector, the power connector, and/or the second fluid connector for connecting the medical device to one or more wires or tubes for connecting with the fluid source, the power source, and/or the second fluid source, respectively. The fluid connector, the power connector, the second fluid connector, or a combination thereof may be a plug, port, socket, tube, opening, orifice, or other passageway configured to diver fluid and power from the corresponding source to the medical device.

The medical device and/or the hand piece may comprise one or more user controls. Movement or manipulation of the one or more user controls may function to move or actuate the introducer; expand or contract one or more expandable members; supply, cease, increase, or decrease a supply or flow of one or more fluids to the expandable member(s); supply, cease, increase, or decrease a supply of power to the one or more heating elements; or a combination thereof.

The one or more user controls may be one or more switches, levers, buttons, triggers, knobs, rotation wheels, or a combination thereof. The one or more user controls may also be a foot pedal in communication with the medical device.

The medical device comprises one or more introducers. The introducer may function to permit a portion of the medical device to be inserted into a patient or the anatomy, while a portion of the device remains outside of the patient or anatomy.

The introducer may be a tubular member. The introducer may be a braided or coiled tube. The introducer may be a tube that is generally smooth on the inside and outside surfaces. The introducer may be an elongated member that extends along a longitudinal axis. The proximal end of the introducer may be connected to the hand piece. The introducer may have a relatively small diameter, on the order of about 10 mm or less, 9 mm or less, 8 mm or less, 7 mm or less, or even 6 mm or less. The diameter of the introducer may be less than 6 mm. Such relatively small sized introducer may be advantageous in minimizing patient trauma during insertion and/or removal of the introducer into and from a body lumen and/or body cavity.

The introducer may be substantially straight and/or may include sections that are substantially straight; may include one or more angles, bends or arcs and/or may include sections that have one or more angles, bends or arcs; or a combination thereof. The introducer may be substantially rigid, substantially flexible, substantially resilient, substantially kink-resistant, or a combination thereof. The introducer may be configured in such a way to allow angular movements and/or can be advanced along a tortuous path within a body lumen and/or body cavity.

The introducer may comprise one or more internal channels or lumen. The channel or lumen may be configured to direct, deliver, and/or withdrawal one or more fluids to and/or from the one or more expandable members or fluid lumen. One or more electrical wires may extend inside or outside of the introducer when extending between the one or more heating elements and the power source.

The medical device may be configured to connect to or with one or more fluid sources. The one or more fluid sources may be referred to herein as a fluid source and/or a second fluid source. The one or more fluid sources may function to contain or store fluid for supply to the medical device. The fluid source may be a container, bag, cartridge, squeeze bottle, or other suitable receptacle. The fluid source may be a pump or a source of pressurized fluid and a control valve. The fluid may be supplied or provided from the fluid source to the medical device (i.e., to the cavity of the expandable member and/or to the fluid cavity) by way of gravity (i.e., an elevated fluid container relative to the medical device), a pump, a hand pump, by squeezing a squeeze bottle or depressing a plunger of a syringe, or a combination thereof. One or more of the fluid sources may be connected to the medical device by way of a connector or port, or may be directly contained within the hand piece or introducer. The fluid may be withdrawn from the medical device (i.e., to the cavity of the expandable member and/or to the fluid cavity) by way of withdrawing a plunger of a syringe, a pump, or a vacuum.

The fluid sources may be referred to herein as a first fluid source and a second fluid source. The first and second fluid sources may be configured to supply the same fluid to the medical device. The first and second fluid sources may be configured to supply different fluid to the medical device.

The fluids may be referred to herein as a first fluid and a second fluid. The first and second fluids may be the same fluids. The first and second fluids may be different fluids.

The first and/or the second fluid may be a gas that is configured to inflate the medical instrument. For example, the first and/or the second fluid may be air, carbon dioxide, nitrogen.

The first and/or the second fluid may be a liquid that is configured to be heated. For example, the first and/or the second fluid may be a sterile liquid, saline, dextrose and/or water solution.

The fluid may be supplied to the medical device to expand or inflate the expandable member, the inner expandable member, the outer expandable member, the fluid cavity, or a combination thereof. The fluid may be configured to absorb heat from the one or more heating elements. The fluid may function to transfer heat from the one or more heating elements to the expandable member for thermal transfer to tissue or anatomy in contact with the outer surface of the expandable member or the outer surface of the outer expandable member.

The medical device may be in electrical communication with one or more power sources. The one or more power sources may function to contain and supply power to the medical device, the one or more heating elements, the one or more fluid supplies, or a combination thereof.

The power source may be an AC power source. The power source may be a standard 120- or 220-volt wall outlet. The power source may be a DC power source. The power source may be located inside of the medical device, like in the hand piece or introducer for example.

The power source may be in electrical communication with the one or more heating elements via one or more wires. By manipulating one or more of the user controls, power may be supplied from the power supply to the one or more heating elements so that the one or more heating elements generate heat. An amount of power supplied to the one or more heating elements may be controlled via the one or more user controls to increase or decrease a heat output from the one or more heating elements and therefore increase or decrease a temperature of the expandable member, the fluid, or both.

The power source may be in electrical communication with the one or more fluid sources. By manipulating one or more of the user controls, power may be supplied from the power supply to the one or fluid sources so that the one or more fluid sources (e.g., a pump) supply fluid to the expandable member, the cavity, the fluid cavity, or a combination thereof.

The medical device comprises one or more expandable members. An expandable member may expand and conform to a body cavity or body cavity. The expandable member may be inflated via one or more fluids from the one or more fluid sources. The expandable member may be a balloon or other ductile, flexible, and/or fluid impermeable member.

An outer surface of the expandable member may be configured to directly contact tissue or the anatomy. The outer surface of the expandable member may include one or more heating elements. The one or more heating elements may be configured to directly contact tissue of the anatomy. The expandable member may be expanded until the one or more heating elements are in contact with the walls of the body cavity so that heat from the heating elements can be transferred to the walls or tissue of the body cavity to effect or ablate the tissue. The one or more heating elements may be resistive heaters that are electrically connected to the power source. The one or more heating elements may be painted, dipped, or applied onto the outer surface of the expandable members. The one or more heating elements may be impregnated into an outer surface of the expandable member.

The expandable member may be inflated or expanded by manipulating one or more of the user controls so that fluid from the one or more fluid source flows into the cavity and expands the expandable member. The expandable member may be deflated or contracted by manipulating one or more of the user controls so that fluid from the one or more fluid source is withdrawn or evacuated from within cavity, which causes the cavity to contract.

The expandable member may be made of a suitable medical grade material, such as a polyurethane, silicone, natural rubber, synthetic rubber, or latex.

In some configurations, the expandable member may comprise an inner expandable member (also referred to herein as an inner member) and an outer expandable member (also referred to herein as an outer member). The inner member may be located within the outer member. Fluid may be contained between the inner and outer member, which may function to protect or reduce chances of the fluid leaking or spilling into the anatomy.

The inner and/or outer member may be made of a suitable medical grade material, such as a polyurethane, silicone, natural rubber, synthetic rubber, or latex. One or both of the inner and outer members may be made of a non-stick material to restrict or prevent the facing surfaces of each of the members from sticking to allow the fluid cavity to be inflated.

The inner and outer members may have a similar shape. The inner and outer members may have a similar size. The outer member may have a size that is slightly larger than the inner member so that when the inner member is inflated inside of the inflated outer member a space, or channel, or passageway, or fluid cavity is defined between the outer surface of the inner member and the inner surface of the outer member.

Between the inner and outer members, the medical device or expandable member may comprise one or more fluid cavities. The fluid cavity may be a path or passageway that is configured to contain fluid. The fluid cavity may be an inner portion of a tubular structure that is defined by the outer surface of the inner member and the inner surface of the outer member. The fluid cavity may include its own walls that are located between the outer surface of the inner member and the inner surface of the outer member. Preferably, the fluid cavity is fluid impermeable so that fluid is contained in the fluid cavity does not leak from inside the fluid cavity into the anatomy or other portions of the expandable member.

The fluid cavity may have a substantially uniform size or uniform cross section or uniform clearance between the surfaces of the inner and outer members defining the fluid cavity.

The fluid cavity may be in fluid communication with one or more of the fluid sources. The fluid cavity may function to receive, store, and/or pass fluid from the one or more fluid sources. The fluid lumen is fluidly isolated from the cavity defined inside of the inner expandable member. This means that fluid inside of the fluid cavity does not and is restricted or prevented from exchanging or mixing with the fluid inside of the cavity, and vice versa.

Fluid may be supplied to the fluid cavity and circulated therein, or may be supplied to the fluid cavity and not circulated therein. The fluid may be supplied to the fluid cavity via a pump, squeeze bottle, or compressing a plunger of a syringe. A pump may not be required to communicate the fluid into the fluid cavity. Fluid may be withdrawn from the fluid cavity via a vacuum or withdrawing a plunger of a syringe.

Supplying fluid to the fluid cavity may assist in expanding or inflating the fluid cavity, the inner member, the outer member, or both. The fluid in the fluid cavity may function to absorb heat from the one or more heating elements and then transfer the heat to the outer surface of the outer member. The heat transferred to the outer surface of the outer member may then be transferred to the anatomy or tissue in contact with the outer surface of the outer member or expandable member.

The medical device may include one or more heating elements. The one or more heating elements may function to generate heat. The one or more heating elements may be painted, sprayed, dipped, pumped, brushed, wiped, deposited, or otherwise applied onto an outer surface of the expandable member, on the outer surface of the inner member, on the inner surface of the outer member, inside the fluid cavity, or a combination thereof. The one or more heating elements may be at least partially impregnated into the outer surface of the expandable member, into the outer surface of the inner member, into the inner surface of the outer member, inside the walls defining fluid cavity, or a combination thereof. The one or more heating elements may be resistive heaters. Use of a resistive heater may be advantageous because it does not require high voltages associated with electrosurgical systems. Moreover, use of a resistive heater does not require a return electrode that need to be positioned somewhere on the body.

The heating elements may function to generate and transfer heat to the tissue or anatomy in contact with or surrounding the outer member, the expandable member, or both. The heating elements may generate and transfer heat to the fluid inside of the fluid cavity, which may then transfer the heat to the outer member and tissue adjacent to the outer surface of the outer member. The heating elements may generate and transfer heat to the fluid inside of the cavity or fluid cavity, which may then transfer the heat to the fluid inside of the fluid cavity, the outer member, and tissue adjacent to the outer surface of the outer member by bringing the expandable member into contact with the tissue or by bringing the expandable member near the tissue.

Figure 1:
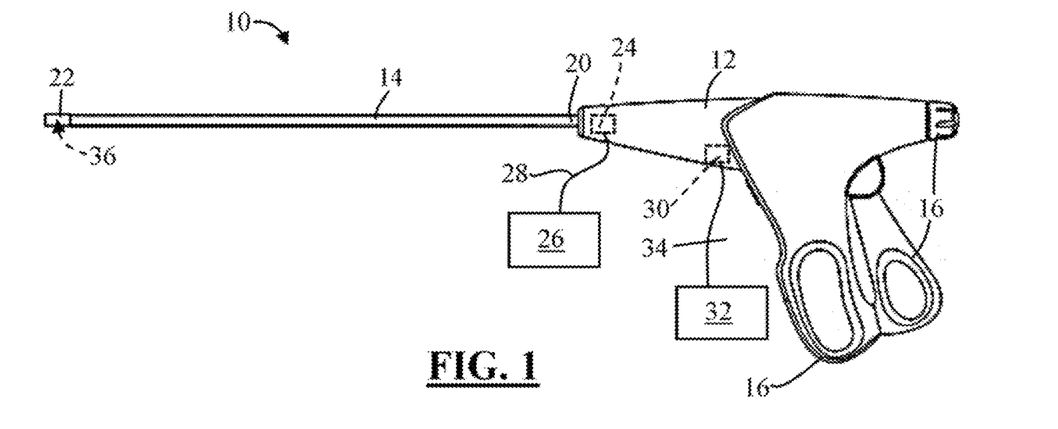
FIG. 1 is a side view of a medical device.

FIG. 1 illustrates a medical device 10. The medical device 10 comprises a hand piece 12 and an introducer 14. The hand piece 12 is configured to be gripped or held by a user. The hand piece 12 comprises one or more user controls 16 for operating, manipulating, and/or using the medical device 10. The introducer 14 has a proximal end 20 connected to the hand piece 12. The introducer 14 comprises a distal end 22.

The medical device 10 comprises a fluid connector 24. The fluid connector 24 is configured to fluidly connect the medical device 10 to a fluid source 26 via one or more fluid lines 28. In some configurations, the fluid source 26 may be contained in the hand piece 12 and in other configurations, the fluid source 26 may be located a distance away from the hand piece 12.

The medical device 10 comprises a power connector 30. The power connector 30 is configured to electrically connect the medical device 10 to a power source 32 via one or more power wires 34. In some configurations, the power source 32 may be contained in the hand piece 12 and in other configurations, the power source 32 may be located a distance away from the hand piece 12.

The medical device 10 comprises an expandable member 36. In FIG. 1, the expandable member 36 is in a collapsed position, and located at least partially inside of the introducer 14.

Figure 2:
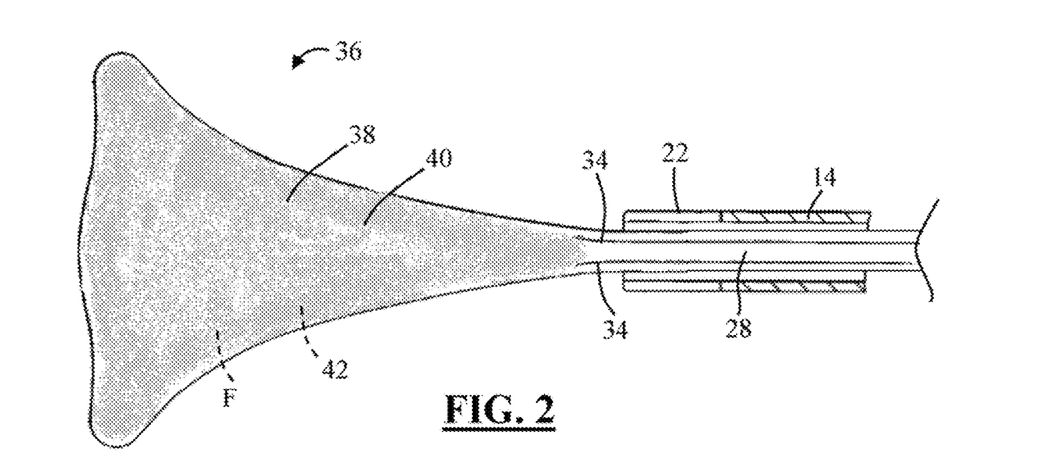
FIG. 2 is a cross-sectional view of a distal end of the medical device of FIG. 1

FIG. 2 illustrates the expandable member 36 in the expanded position, where the expandable member 36 is at least partially extended from the distal end 22 of the introducer 14.

The expandable member 36 comprises a balloon that is configured to conform to an inside of a body cavity or body lumen. The body cavity can be any body cavity. The body cavity may be a uterus.

The expandable member 36 comprises an outer surface 38. One or more heating elements 40 may be disposed on the outer surface 38 of expandable member 36 and/or may be impregnated into the outer surface 38 of the expandable member 36. In some configurations, the one or more heating elements 40 may be disposed on an inside surface of the expandable member 36 (i.e., inside of the cavity 42). The one or more heating elements 40 are electrically connected to the one or more power wires 34 that are electrically connected to the power source 32 (FIG. 1).

The expandable member 36 comprises an inner portion or cavity 42. The cavity 42 is in fluid communication with the fluid connector 24, which is fluidly connected to the one or more fluid lines 28, which are fluidly connected to the fluid source 26 (FIG. 1).

Referring to FIGS. 1 and 2, during a medical procedure, the introducer 14 can be configured for insertion or placement into a body cavity or body lumen while the expandable member 36 is in the collapsed position and located at least partially inside of the introducer 14 (FIG. 1).

Before, during, or after insertion or placement of the introducer 14 into the body cavity, one or more of the user controls 16 can be manipulated so that fluid F from the fluid source 26 is supplied to the cavity 42 of the expandable member 36 via the one or more fluid lines 28. Supplying the fluid F from the fluid source 26 into the cavity 42 functions to inflate the expandable member 36 into an inflated position illustrated in FIG. 2.

The one or more fluid lines 28 may be one or more single or individual lines or passageways configured to inflate the expandable member 36. This means that the fluid is not circulated inside the expandable member 36 or provided into and then withdrawn out of the expandable member 36 while the expandable member 36 remains inflated. Instead, the one or more fluid lines 28 may be configured to deliver the fluid to the expandable member 36 to inflate the expandable member. After use, the one or more fluid lines 28 may then be configured to withdrawal the fluid from inside the expandable member 36 to deflate the expandable member. In some configurations, however, the one or more fluid lines 28 may be configured to circulate the fluid inside of the expandable member 36 while the expandable member 36 remains inflated. This means that the fluid moves inside of the expandable member 36 while the expandable member 36 remains inflated and/or there is an exchange of the fluid supplied to and from the expandable member 36 while the expandable member 36 remains inflated.

It is understood that because the expandable member 36 is configured to conform to a body cavity during or after inflation, and because the body cavity can be virtually any size and shape, the inflated expandable member 36 can have virtually any shape. In the example of FIG. 2, the expandable member 36 is shown conforming to a shape of an inside of a uterus. The expandable member 36 can be inflated until at least a portion, but preferably most or all of the outer surface 38 of the expandable member 36 is in contact with, or at least in close contact with, the walls or anatomy defining the body cavity.

Before, during, or after the expandable member 36 is in an expanded configuration, one or more user controls 16 can be manipulated so that power from the power source 32 is communicated to the one or more heating elements 40 via the one or more power wires 34. This causes the one or more heating elements 40 to generate heat. The heat generated by the heating elements 40 may cause the outer surface 38 of the expandable member 36 to heat up. The heat generated by the heating elements 40 may cause the fluid F inside of cavity 42 to heat up. The heat generated by the heating elements 40 may cause the inner surface of the expandable member 36 to heat up. The one or more heating elements 40 may be resistive heaters. During use, the heat generated by the one or more heating elements 40 and/or from the heated outer surface 38 of the expandable member 36 is then transferred to the walls or anatomy defining the body cavity by bringing the outer surface 38 of the expandable member 36 near the walls or anatomy defining the body cavity and/or by bringing the outer surface 38 of the expandable member 36 into actual contact with the walls or anatomy defining the body cavity to treat or ablate the walls or structure thereof.

During or after completion of the medical procedure, one or more of the user controls 16 can be manipulated to cease providing the power to the one or more heating elements 40 so that the heat elements 40 cease generating heat. During or after completion of the medical procedure, one or more of the user controls 16 can be manipulated to release or draw or evacuate the fluid F from inside of the cavity 42 so that the expandable member 36 at least partially collapses. During or after completion of the medical procedure, one or more of the user controls 16 can be manipulated so that the expandable member 36 is at least partially drawn back into a distal end 22 of the introducer 14. During or after completion of the medical procedure, the medical device 10 or introducer 14 can be removed or withdrawn from the body cavity.

Figure 3:
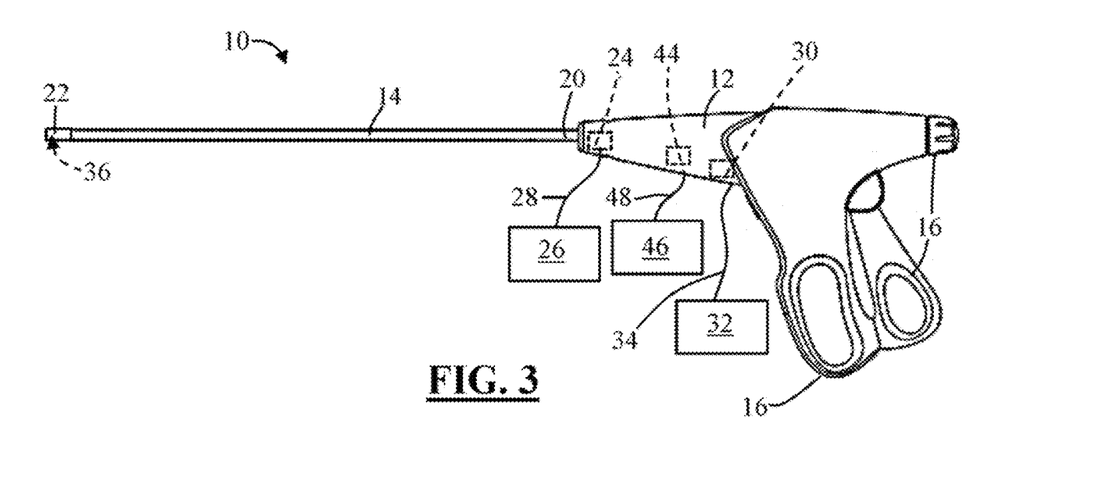
FIG. 3 is a side view of a medical device.

FIG. 3 illustrates a medical device 10. The medical device 10 comprises a hand piece 12 and an introducer 14. The hand piece 12 is configured to be gripped or held by a user. The hand piece 12 comprises one or more user controls 16 for operating, manipulating, and/or using the medical device 10. The introducer 14 has a proximal end 20 connected to the hand piece 12. The introducer 14 comprises a distal end 22.

The medical device 10 comprises a fluid connector 24. The fluid connector 24 may also be referred to herein as a first fluid connector. The fluid connector 24 is configured to fluidly connect the medical device 10 to a fluid source 26 via one or more fluid lines 28. The fluid source 26 may be referred to herein as a first fluid source 26. In some configurations, the fluid source 26 may be contained in the hand piece 12. In other configurations, the fluid source 26 may be located a distance away from the hand piece 12. The fluid source 26 contains fluid F, which may also be referred to herein as a first fluid F.

The medical device 10 comprises a power connector 30. The power connector 30 is configured to electrically connect the medical device 10 to a power source 32 via one or more power wires 34. In some configurations, the power source 32 may be contained in the hand piece 12. In other configurations, the power source 32 may be located a distance away from the hand piece 12.

The medical device 10 comprises a second fluid connector 44. The second fluid connector 44 is configured to fluidly connect the medical device 10 to a second fluid source 46 via one or more second fluid lines 48. In some configurations, the second fluid source 46 may be contained in the hand piece 12. In other configurations, the second fluid source 46 may be located a distance away from the hand piece 12. The second fluid source 46 contains second fluid 2F.

The medical device 10 comprises an expandable member 36. In FIG. 3, the expandable member 36 is in a collapsed position, and is located at least partially inside of the distal end 22 of the introducer 14.

Figure 4:
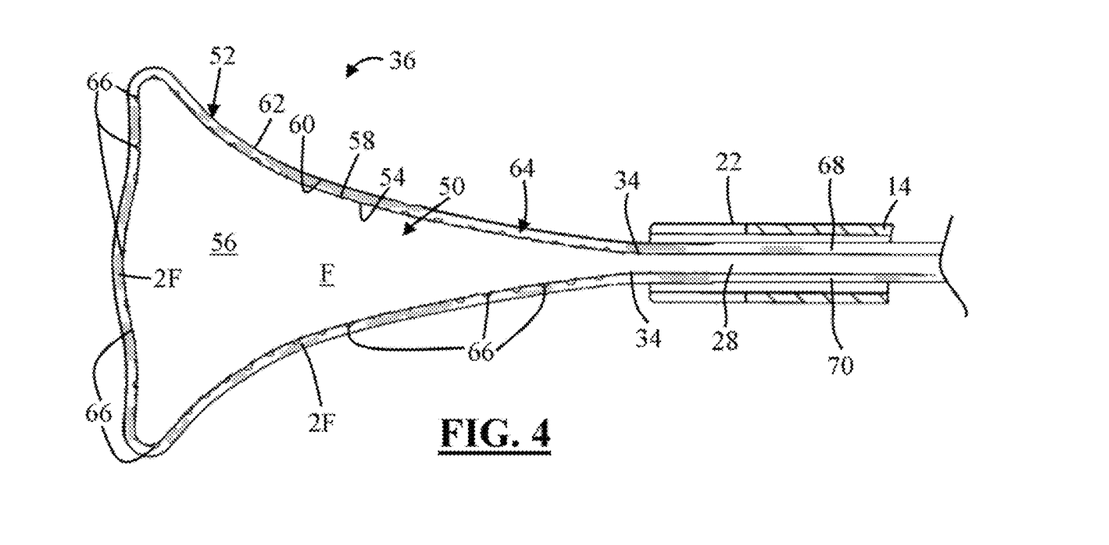
FIG. 4 is a cross-sectional view of a distal end of the medical device of FIG. 3.

FIG. 4 illustrates the expandable member 36 in the expanded position and at least partially extending from the distal end 22 of the introducer 14.

The expandable member 36 comprises a balloon that is configured to conform to an inside of a body cavity. For example, the body cavity may be a uterus.

The expandable member 36 comprises an inner expandable member 50 located inside of an outer expandable member 52. The inner expandable member 50 comprises an inner surface 54 defining a cavity 56 inside the inner expandable member 50. The inner expandable member 50 comprises an outer surface 58.

The cavity 56 is in fluid communication with the fluid connector 24, which is fluidly connected to the one or more fluid lines 28, which are fluidly connected to the fluid source 26 (FIG. 3) containing the first fluid F.

The outer expandable member 52 comprises an inner surface 60 located adjacent to the outer surface 58 of the inner expandable member 50. The outer expandable member 52 comprises an outer surface 62.

The expandable member 36 comprises a fluid cavity 64 defined between the inner expandable member 50 and the outer expandable member 52. The fluid cavity 64 is defined by or between the outer surface 58 of the inner expandable member 50 and the inner surface 60 of the outer expandable member 52. The fluid cavity 64 is in fluid communication with the second fluid source 46 that contains the second fluid 2F via the one or more second fluid lines 48.

The fluid cavity 64 comprises a first fluid opening 68 and a second fluid opening 70. The first fluid opening 68 may be a supply or delivery opening or line where fluid is supplied or delivered into the fluid cavity 64, and the second fluid opening 70 may be an output or withdrawal opening or line where the fluid is removed or withdrawn from the fluid cavity 64, or vice versa. The fluid openings 68, 70 are in fluid communication with the one or more second fluid lines 48. The second fluid 2F can be supplied into the fluid cavity 64 through one of the fluid openings 68, 70 and then withdrawn from the fluid cavity 65 via the other of the fluid openings 68, 70. The second fluid 2F may be circulated inside of the fluid cavity 64 by suppling the second fluid 2F into the fluid cavity 64 and then withdrawing the second fluid 2F via the fluid openings 68, 70. In other configurations, the second fluid 2F can be supplied into the fluid cavity 64 through one of the fluid openings 68, 70 and then withdrawn from the fluid cavity 65 via the same fluid opening 68, 70.

The fluid cavity 64 is fluidly isolated from the cavity 56. This means that fluids contained or provided in each of the cavity 64 and cavity 56 are restricted or prevented from mixing inside of the medical device 10. Preferably the fluids are restricted or prevented from mixing because the fluids are different. For example, the first fluid F supplied into the cavity 56 may be carbon dioxide, nitrogen, air, (or other such gases) and the second fluid 2F supplied into the fluid cavity 64 may be saline.

The medical device 10 comprises one or more heating elements 66. The one or more heating elements 66 are located inside of the expandable member 36. The one or more heating elements 66 may be located inside of the fluid cavity 64. The one or more heating elements 66 may be disposed on the outer surface 58 of the inner expandable member 50, disposed on the inner surface 60 of the outer expandable member 52, impregnated on one or both of the surfaces 58, 60, or a combination thereof. The one or more heating elements 66 are in electrical communication with the power source 32 via the one or more power wires 34. The one or more heating elements 66 may be resistive heaters. The one or more heating elements 66 may be configured to generate heat. The heat generated by the heating elements 66 may be configured to heat up or increase a temperature of the second fluid 2F that is located inside of the fluid cavity 64 and/or circulated inside of the fluid cavity 64.

The volume of the second fluid 2F that is heated inside of the fluid cavity 64 is less than the volume of the fluid located inside of the cavity 42 of the expandable member 36 in FIG. 2. Advantageously, this means that the time required to heat the second fluid 2F is less than the time required to heat the fluid located inside of the cavity 42 of the expandable member 36 in FIG. 2. Moreover, the time required to fill and withdrawal the second fluid 2F from the fluid cavity 64 is less than the time required to fill and withdrawal the fluid located inside of the cavity 42 of the expandable member 36 in FIG. 2.

Referring to FIGS. 3 and 4, during a medical procedure, the introducer 14 can be configured for insertion or placement into a body cavity while the expandable member 36 is in the collapsed position at least partially inside of the introducer 14 (FIG. 3).

Before, during, or after insertion or placement into the body cavity, one or more of the user controls 16 can be manipulated so that fluid F from the fluid source 26 is supplied to the cavity 56 of the expandable member 36 via the one or more fluid lines 28. Supplying the first fluid F from the fluid source 26 into the cavity 56 functions to inflate the inner expandable member 50, which causes the outer expandable member 52 to also expand, even though the first fluid F is contained only within the cavity 56 of the inner expandable member 50.

The one or more fluid lines 28 may be one or more single or individual lines or passageways configured for inflating the expandable member 36. This means that the first fluid F is not circulated inside the expandable member 36 or provided into and then withdrawn out of the expandable member 36 while the expandable member 36 remains inflated. Instead, the one or more fluid lines 28 may be configured to deliver the first fluid F to the expandable member 36 to inflate the expandable member. The one or more fluid lines 28 may then be configured to withdrawal the first fluid F from inside the expandable member 36 to deflate the expandable member. In some configurations, however, the one or more fluid lines 28 may be configured to circulate the first fluid F inside of the expandable member 36 while the expandable member 36 remains inflated. This means that the first fluid F moves inside of the expandable member 36 while inflated and/or there is an exchange of the first fluid F supplied to and from the expandable member 36 while the expandable member 36 remains inflated.

The expandable member 36 can be expanded into the exemplary position illustrated in FIG. 4. It is understood that because the expandable member 36 is configured to conform to a body cavity and because the body cavity can be virtually any size and shape, the inflated expandable member 36 can have virtually any shape. In the example of FIG. 4, the expandable member 36 confirms to a uterus. The expandable member 36 can be inflated until at least a portion, but preferably most or all of the outer surface 62 of the outer expandable member 52 is in contact with the walls or anatomy defining the body cavity.

Before, during, or after the expandable member 36 is in an expanded configuration and generally or mostly in contact with the wall or anatomy defining the body cavity, one or more user controls 16 can be manipulated so that fluid 2F from the second fluid source 46 is communicated into the fluid cavity 64 via the one or more second fluid lines 48. Because the expandable members are 50, 52 are fluid impermeable, the fluid 2F is contained within the fluid cavity 64 and therefore fluidly isolated from the fluid in the cavity 56. A sufficient amount of the fluid 2F can be communicated into the fluid cavity 64 to fill, or at least partially fill, the fluid cavity 64.

Because the fluid cavity 64 and the cavity 56 are separate and fluidly isolated from one another (i.e., the first fluid F and the second fluid 2F do not mix), the second fluid 2F can be flushed or withdrawn from the fluid cavity 64 while the first fluid F remains inside of the cavity 56 so that the general shape of the expandable member 36 is maintained. The second fluid 2F can also be circulated inside of the fluid cavity 64 by supplying and withdrawing the second fluid 2F via one or both of the fluid openings 68, 70, while the first fluid F remains inside of the cavity 56 so that the general shape of the expandable member 36 is maintained.

The fluid 2F is configured to be heated by the one or more heating elements 66. It may be preferred that the fluid 2F is not circulated inside the cavity 64 during a medical procedure. This means that the one or more fluid lines 48 may be one or more single or individual lines or passageways configured for supplying the fluid 2F into the fluid cavity 64. This means that the fluid is not circulated inside the fluid cavity 64 or provided into and then withdrawn out of the fluid cavity 64 while the fluid cavity 64 remains inflated. Instead, the one or more fluid lines 48 may be configured to deliver the fluid 2F to the fluid cavity 64 to inflate the fluid cavity 64. The one or more fluid lines 48 may then be configured to withdrawal the fluid 2F from inside the fluid cavity 64 to deflate the fluid cavity 64. In some configurations, however, the one or more fluid lines 48 may be configured to circulate the fluid 2F inside of the fluid cavity 64 while the fluid cavity 64 remains inflated. This means that the fluid 2F moves inside of the fluid cavity 64 while inflated and/or there is an exchange of the fluid 2F supplied to and from the fluid cavity 64 while the fluid cavity 64 remains inflated.

Before, during, or after the expandable member 36 is in an expanded configuration and/or before, during, or after the fluid 2F is supplied into the fluid cavity 64, one or more user controls 16 can be manipulated so that power from the power source 32 is communicated to the one or more heating elements 40 via the one or more power wires 34. This causes the one or more heating elements 66 to generate heat. The heat from the heating elements 66 is transferred to the fluid 2F located in the fluid cavity 64 so that a temperature of the fluid 2F increases. The heat from the fluid 2F is then transferred to the outer expandable member 52 or the outer surface 60 of the outer expandable member 52. The heat at the outer expandable member 52 is then transferred to the walls or anatomy defining the body cavity treat or ablate the walls or anatomy by way of contact between the warm or heated outer expandable member 52 and the walls or anatomy.

After completion of the medical procedure, one or more of the user controls 16 can be manipulated to at least partially withdrawal the fluid from inside of the cavity 42 and/or from inside of the fluid cavity 64 so that the expandable member 36 at least partially collapses. The medical device 10 or introducer 14 can then be removed or withdrawn from the body cavity. One or more of the user controls 16 can be manipulated to cease providing power to the one or more heating elements 40 before, during, or after the expandable member 36 is collapsed and/or before during or after the medical device 10 or introducer 14 is withdrawn from the body cavity.

LISTING OF REFERENCE NUMERALS 10 medical device
12 hand piece
14 introducer
16 user controls
18 longitudinal axis
20 proximal end
22 distal end
24 fluid connector
26 fluid source
28 fluid line
30 power connector
32 power source
34 power wire
36 expandable member
38 outer surface of expandable member 36
40 heating element
42 cavity of expandable member 36
44 second fluid connector
46 second fluid source
48 fluid line
50 inner expandable member
52 outer expandable member
54 inner surface of inner expandable member 50
56 cavity of inner expandable member 50
58 outer surface of inner expandable member 50
60 inner surface of the outer expandable member 52
62 outer surface of the outer expandable member 52
64 fluid cavity
66 heating element
68 fluid line
70 fluid line The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device comprising:
an expandable member comprising an inner expandable member having an outer surface and an outer expandable member having an inner surface;
a first fluid cavity located between the inner expandable member and the outer expandable member, wherein the first fluid cavity includes walls that are fluid impermeable;
a second fluid cavity, in an interior region defined within an inner surface of the inner expandable member and separated therefrom by a fluid impermeable wall of the walls of the first fluid cavity, the second fluid cavity in fluid communication with an inflation fluid source;
a first resistive heating element impregnated into the inner expandable member outer surface to resistively heat a fluid confined within the first fluid impermeable fluid cavity; and
a second resistive heating element impregnated into the outer expandable member inner surface to resistively heat the fluid confined within the first fluid impermeable fluid cavity.

2. The medical device according to claim 1, wherein the first fluid cavity is free of fluid communication with the second fluid cavity.

3. The medical device according to claim 1, wherein the expandable member is configured to expand and generally conform to an inside of a uterus.

4. The medical device according to claim 1, wherein the first fluid cavity comprises a fluid inlet for delivering a fluid into the first fluid cavity and a fluid outlet for withdrawing a fluid from the first fluid cavity.

5. A medical device comprising:
an expandable member comprising a cavity, an inner expandable member having an outer surface, and an outer expandable member having an inner surface;
a fluid impermeable fluid cavity located inside of the cavity, the fluid impermeable fluid cavity being configured to connect to a fluid source to supply a fluid into the fluid impermeable fluid cavity;
a first resistive heating element impregnated into the inner expandable member outer surface and a second resistive heating element impregnated into the outer expandable member inner surface to resistively heat a fluid confined within the fluid impermeable fluid cavity, the heating element being configured to connect to a power source to supply power to the heating element to generate heat and increase a temperature of the fluid inside of the fluid impermeable fluid cavity.

6. The medical device according to claim 5, wherein the fluid cavity comprises a fluid inlet for delivering a fluid into the fluid cavity and a fluid outlet for withdrawing a fluid from the fluid cavity.

7. The medical device according to claim 5, element is a resistive heater.

8. The medical device according to claim 5, wherein the cavity is fluidly isolated from the fluid cavity.

9. The medical device according to claim 5, wherein the cavity is in fluid communication with a second fluid source.

10. The medical device according to claim 5, wherein the expandable member is configured to expand and conform to an inner surface of a body cavity.

11. A method comprising:
inserting the medical device of claim 7 in to a body cavity;
inflating the cavity;
delivering the fluid into the fluid cavity; and
supplying power to the heating element to generate heat to increase a temperature of the fluid.

12. The method of claim 11, wherein heat generated by the increase of the temperature of the fluid is transferred to tissue surrounding the body cavity.

13. The method of claim 11, wherein the fluid cavity comprises a fluid inlet for delivering the fluid into the fluid cavity and a fluid outlet for withdrawing the fluid from the fluid cavity.

14. A medical device comprising:
an expandable member comprising an inner expandable member having an outer surface and an outer expandable member having an inner surface, wherein the expandable member is configured to expand to generally conform to an inside of a uterus;
a first fluid cavity located between the inner expandable member and the outer expandable member, wherein the first fluid cavity includes walls that are fluid impermeable;
a second fluid cavity, in an interior region defined within an inner surface of the inner expandable member and separated therefrom by a fluid impermeable wall of the walls of the first fluid cavity, the second fluid cavity in fluid communication with an inflation fluid source;
a first resistive heating element impregnated into the inner expandable member outer surface to resistively heat a fluid confined within the first fluid impermeable fluid cavity; and
a second resistive heating element impregnated into the outer expandable member inner surface to resistively heat the fluid confined within the first fluid impermeable fluid cavity.

* * * * *

UNITED STATES PATENT AND TRADEMARK OFFICE
CERTIFICATE OF CORRECTION

Page 1 of 1

PATENT NO. : 11,832,869 B2
APPLICATION NO. : 16/291140
DATED : December 5, 2023
INVENTOR(S) : Murdeshwar et al.

It is certified that error appears in the above-identified patent and that said Letters Patent is hereby corrected as shown below:

In the Claims

In Column 14, Line 19, in Claim 7, before "element", insert --wherein the heating--

In Column 14, Line 29, in Claim 11, delete "claim 7 in to" and insert --claim 7, into-- therefor Signed and Sealed this
Eleventh Day of February, 2025

Coke Morgan Stewart
*Acting Director of the United States Patent and Trademark Office*